(12) United States Patent
Leitner et al.

(10) Patent No.: US 7,319,897 B2
(45) Date of Patent: Jan. 15, 2008

(54) LOCALIZATION DEVICE DISPLAY METHOD AND APPARATUS

(75) Inventors: François Leitner, Uriage (FR); François Boux de Casson, Grenoble (FR)

(73) Assignee: Aesculap AG & Co. KG, Tuttlingen (DE)

( * ) Notice: Subject to any disclaimer, the term of this patent is extended or adjusted under 35 U.S.C. 154(b) by 768 days.

(21) Appl. No.: 10/307,732

(22) Filed: Dec. 2, 2002

(65) Prior Publication Data
US 2004/0105086 A1 Jun. 3, 2004

(51) Int. Cl.
*A61B 5/05* (2006.01)

(52) U.S. Cl. .............. 600/424; 600/112; 600/117; 600/126; 600/168; 600/407; 600/414; 600/426; 600/463

(58) Field of Classification Search ............ 600/426, 600/414, 463, 168
See application file for complete search history.

(56) References Cited

U.S. PATENT DOCUMENTS

| | | | |
|---|---|---|---|
| 5,037,426 A * | 8/1991 | Goble et al. .............. 606/96 |
| 5,564,437 A | 10/1996 | Bainville et al. |
| 5,638,819 A | 6/1997 | Manwaring et al. |
| 6,155,973 A * | 12/2000 | Howes et al. .............. 600/112 |
| 6,385,475 B1 | 5/2002 | Cinquin et al. |
| 6,466,815 B1 * | 10/2002 | Saito et al. .............. 600/429 |
| 2001/0016684 A1 * | 8/2001 | Shahidi .............. 600/429 |

FOREIGN PATENT DOCUMENTS

WO    WO01/39683    6/2001

\* cited by examiner

*Primary Examiner*—Brian L. Casler
*Assistant Examiner*—James Kish
(74) *Attorney, Agent, or Firm*—Synnestvedt & Lechner LLP

(57) ABSTRACT

A localization device display method and apparatus for displaying different views, e.g., of different magnification, based on the proximity of the tip of a pointer tracked by the localization device to a reference location identified by the localization device. The display method and apparatus may be incorporated into a surgical navigation system for use in identifying a location for drilling a femoral tunnel in an ACL repair procedure.

29 Claims, 4 Drawing Sheets

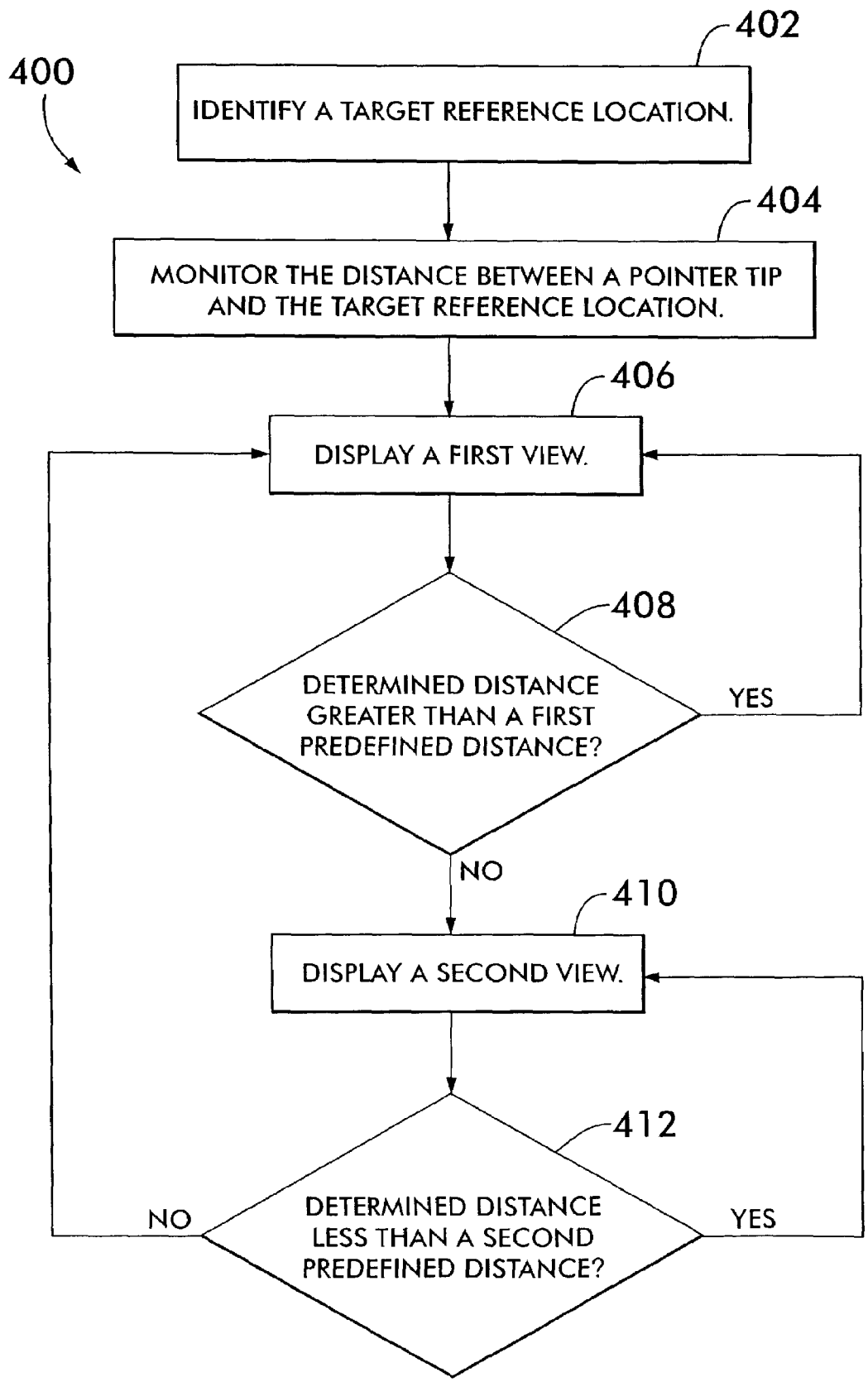

LOCALIZATION DEVICE DISPLAY METHOD AND APPARATUS

FIELD OF THE INVENTION

The present invention relates to medical instruments and, more particularly, to a method and apparatus for displaying localization device information.

BACKGROUND OF THE INVENTION

Localization devices have been developed to assist surgeons in performing surgical procedures, e.g., anterior cruciate ligament (ACL) repair procedures. When utilized in an ACL procedure, markers are attached to bones that are observable by a stereoscopic camera system connected to a data processing system that records the positions of the markers in space to establish a coordinate reference system relative to each bone. Additional markers are used to palpate (touch) specific landmarks on the bones in order to ascertain the position of the landmarks in the coordinate reference systems of the bones. A monitor is used to display a representation of the bones that is based on the coordinate reference system and the landmarks for use in guiding a surgeon during the procedure. A description of one particular localization device is described in U.S. Pat. No. 6,385,475 to Cinquin et al., incorporated fully herein by reference.

In one step of the ACL procedure, after a tibial tunnel for receiving one end of a replacement ACL is drilled, the localization device calculates a reference location on a surface of a femur to drill a hole, i.e., a femoral tunnel, in which the other end of the ACL will be attached. Particularly, the femoral tunnel should be placed in a position that will result in the best isometricity for the repaired ACL (i.e., the smallest distance variation between the repaired ACL insertion points in the tibia and femur over the entire range of extension and flexion of the knee joint). A reference location based solely on best isometricity may not be the optimum location for the femoral tunnel. Other criteria must be considered in determining the optimum location of the femoral tunnel. Other points on the femur in the vicinity of the point of greatest isometricity may provide adequate isometricity. Accordingly, a surgeon typically selects an optimum location for the femoral tunnel in the vicinity of the reference location that provides the best compromise between all criteria.

Presently, the surgeon selects the optimum location for the femoral tunnel with the assistance of the localization device. The surgeon positions the tip of a pointer in the general vicinity of the reference location based on instructions from the localization device and his/her knowledge of the procedure. The pointer has a marker that can be tracked by the localization device. The localization device is programmed with data indicating the orientation and position of the pointer tip relative to the marker. By observing the marker, the localization device can determine the position of the pointer tip relative to the surface of the femur.

The localization device displays on a monitor a magnified visual representation of a portion of the surface of the femur including an indicator representing the position of the pointer tip on the surface of the femur. In addition, the localization device displays the isometricity for the position on the femur corresponding to the pointer tip along with information related to other well known criteria for determining the optimum location for the femoral tunnel. Initially, using the visual representation and the displayed isometricity as a guide, the surgeon moves the pointer tip over the surface of the femur to physically locate an area with good isometricity, which will be located in an area surrounding the reference location of greatest isometricity. The surgeon then moves the pointer tip in the general vicinity of the reference location, e.g., within 10 mm, while observing isometricity and other criteria information feedback from the localization device. Finally, the surgeon selects the optimum location for the femoral tunnel based on the observed feedback.

To provide the necessary degree of precision to locate the area in the near vicinity of the reference location and observe points in the general vicinity of the reference location, the magnified visual representation area displayed by the localization device represents an area surrounding the tip of the pointer that is approximately a centimeter in diameter. The actual surface of the bone is relatively large in comparison to the display area and it is difficult to determine the direction the pointer needs to move to reach the reference location, requiring trial and error on the part of the surgeon. Thus, it is cumbersome and time consuming for the surgeon to locate the reference location using the magnified display area.

Accordingly, there is a need for display methods and apparatus to assist in locating reference locations. The present invention fulfills this need among others.

SUMMARY OF THE INVENTION

The present invention provides for display methods and apparatus that overcome the aforementioned problem by displaying different views based on the proximity of an instrument tracked by a localization device to a reference location identified by the localization device. The localization device displays different views, e.g., of different magnifications, based on the distance between the reference location identified by the localization device and the tip of the pointer being tracked by the localization device. By displaying different views based on the proximity of the pointer tip to the reference location, views are presented that may assist a surgeon in locating efficiently the reference location. For example, the surgeon may be presented initially with a coarse view for use in coarsely positioning the pointer tip and, when the pointer tip is within a specified distance of the reference location, the surgeon may be presented with a fine view for use in finely positioning the pointer tip. The present invention is particularly well suited, although not exclusively so, for use during an ACL repair procedure to enable a surgeon to efficiently select an optimum location for drilling a femoral tunnel.

One aspect of the present invention is a method of generating a display for use with a localization device, the localization device identifying a reference location. The method includes monitoring the distance between a pointer tip and the reference location and displaying one of a plurality of views based on the monitored distance.

Another aspect of the invention is a localization device, the localization device identifying a reference location. The localization device includes sensors for tracking a marker associated with a pointer tip, a monitor, and a computer coupled to the sensors and the monitor for monitoring the distance between the pointer tip and the reference location and selecting a view for display on the monitor from a plurality of views based on the monitored distance.

Another aspect of the invention is a computer program product for displaying views in a localization device that identifies a reference location. The computer program product includes computer readable program code embodied in a computer readable medium. The computer readable program code includes computer readable program code for monitoring the distance between a pointer tip and the reference location and computer readable program code for displaying one of a plurality of views based on the monitored distance.

BRIEF DESCRIPTION OF THE DRAWINGS

FIG. 4 is a flow chart depicting the steps for selecting which view to display in accordance with the present invention.

DETAILED DESCRIPTION OF THE INVENTION

Figure 1:
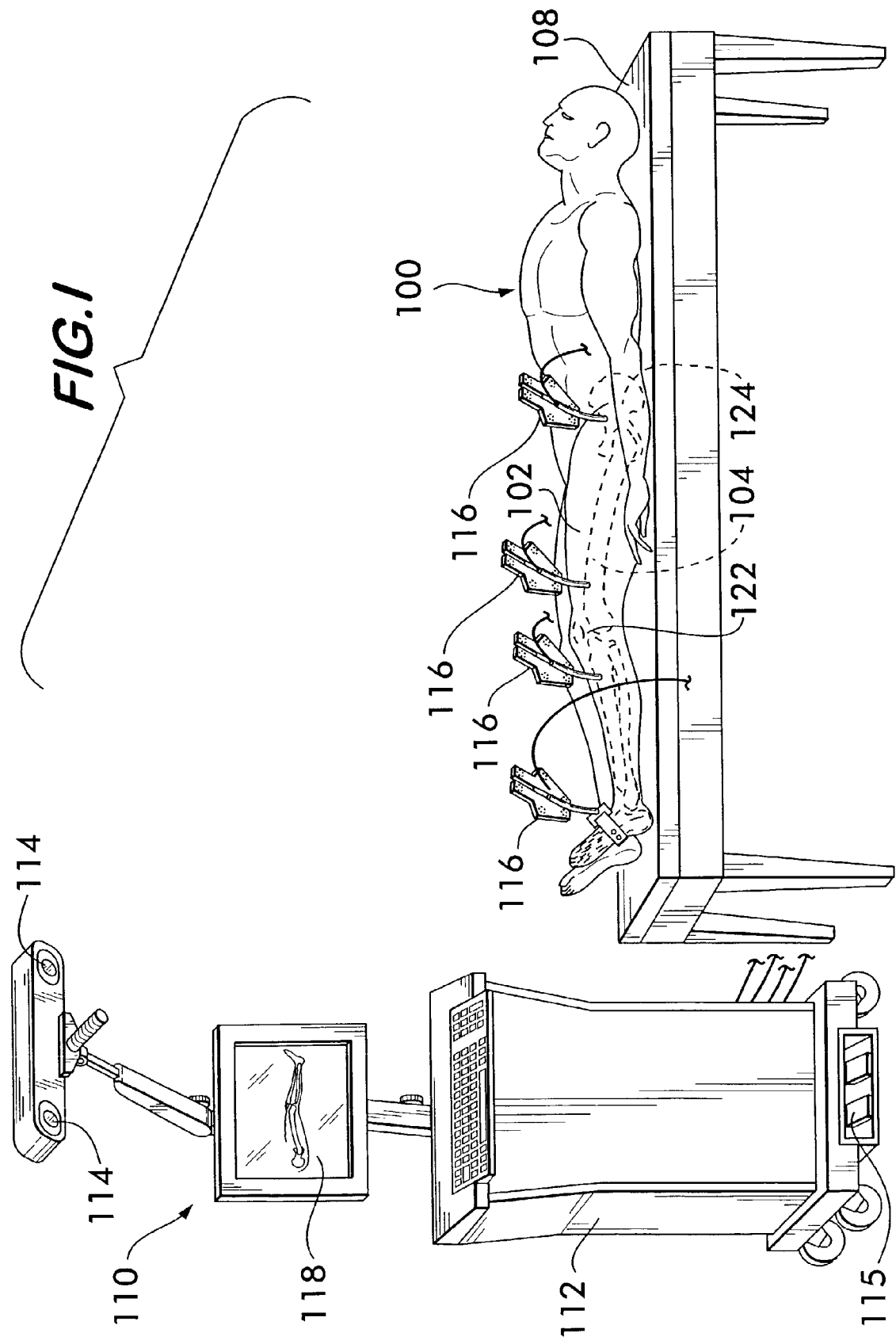
FIG. 1 is an illustration of a patient about to undergo an ACL repair procedure utilizing a localization device in accordance with the present invention.

FIG. 1 depicts a localization device 110 in which the method of the present invention may be employed. For descriptive purposes, a preferred embodiment of the present invention will be described in connection with selecting the location for a tunnel within a femur 104 during an ACL repair procedure after a tibial tunnel for connecting a replacement ACL is drilled.

In FIG. 1, a patient 100, who is to undergo an ACL repair procedure on a leg 102 is illustrated schematically lying on an operating table 108. The localization device 110 includes a computer 112 loaded with software for surgical navigation, sensors 114, e.g., cameras, capable of detecting markers 116, and a monitor 118 for displaying surgical navigation information to a surgeon to help the surgeon select a location for drilling the femoral tunnel. The sensors 114 are positioned above and laterally from the patient 100 so that the patient's leg 102 is in the field of view of the sensors 114. In general, the markers 116 are fixedly mounted on bones and surgical instruments so that the localization device 110 can track the exact location and orientation of the bones and surgical instruments to which they are mounted to determine a frame of reference. A description of a suitable localization device 110 is found in U.S. Pat. No. 6,385,475 to Cinquin et al., having a common inventor and commonly assigned to the same entity as the present application.

Figure 2:
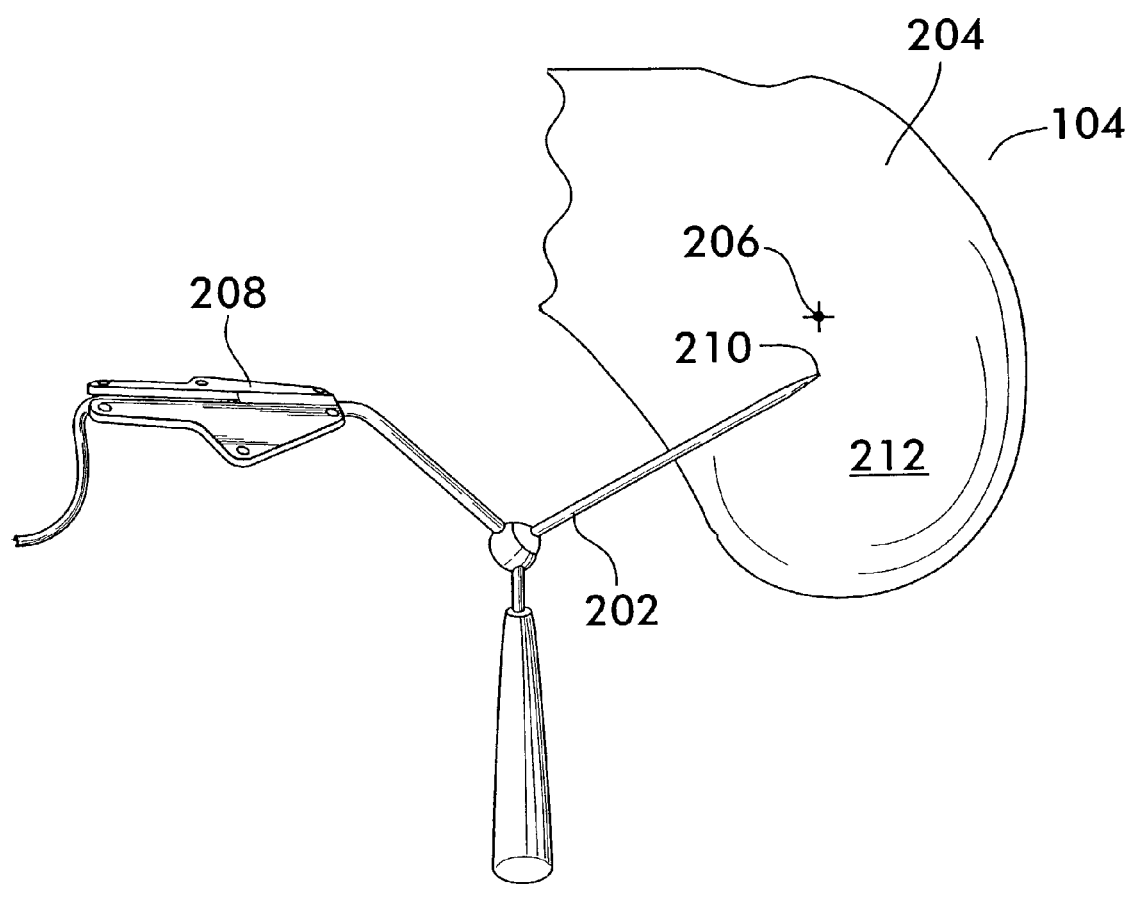
FIG. 2 is a close-up view of a portion of the femur of FIG. 1 and a pointer device for palpating points on the femur in accordance with the present invention.

FIG. 2 depicts a pointer 202 and a portion 204 of the femur 104 of FIG. 1 with like elements being identically numbered. The pointer 202 is capable of receiving a marker 208 for tracking by the localization device 110. The localization device is programmed with data indicating the orientation and position of the pointer tip 210 relative to the marker 208. By observing the marker 208, the localization device 110 can determine the position and orientation of the pointer tip 210 relative to other points known to the localization device 110. It will be understood by those skilled in the art that the pointer 202 may be essentially any device capable of identifying a point in space and that the pointer tip 210 may be essentially any identifiable position associated with that device.

Initially, a reference location 206 is identified by the localization device 110. For descriptive purposes, the reference location 206 is illustratively depicted on the femur portion 204, however, it will be understood that an indication of the reference location 206 is not physically located on the femur 104. Preferably, the reference location 206 is identified with reference to a tibial tunnel (not shown) that was navigated previously in a known manner using the localization device 110, which retains information related to the tibial tunnel such as the tibial ACL insertion location. Utilizing the localization device, the reference location 206 may be identified by, first, digitizing an area on the femur 104 that is conventionally used as a replacement ACL femur insertion location, i.e., an area within the intercondylar fossa 212 of the femur 104, and developing a continuous representation of that area using known interpolation techniques. Second, the trajectory of the ACL tibial insertion location in the femur frame of reference is recorded during flexion and extension of the leg 102 (FIG. 1). Finally, for each point in the continuous representation, a value equivalent to the difference in distance between that point and the trajectory of the ACL tibial insertion area in flexion and in extension is calculated and the point corresponding to the smallest difference (i.e., the best isometricity) is identified as the reference location. One method for identifying a reference location may be found in U.S. Pat. No. 5,564,437 to Bainville et al. entitled Method and System for Determining the Fixation Point on the Femur of a Crossed Ligament of the Knee, incorporated fully herein by reference.

Figure 3A:
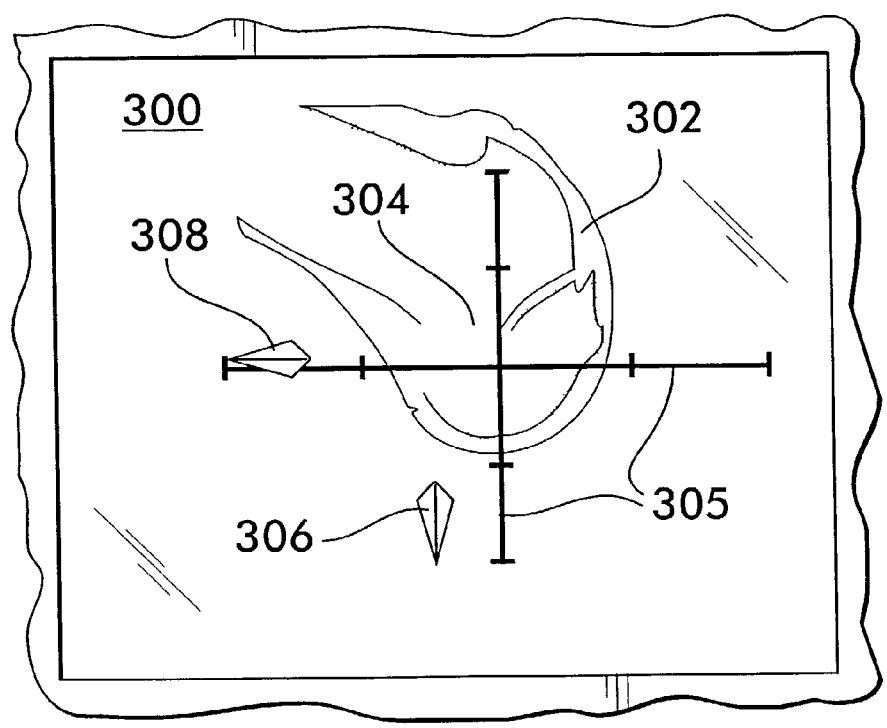
FIGS. 3A and 3B depict a coarse view and a fine view of the femur of FIG. 2, respectively, in accordance with the present invention.
Figure 3B:
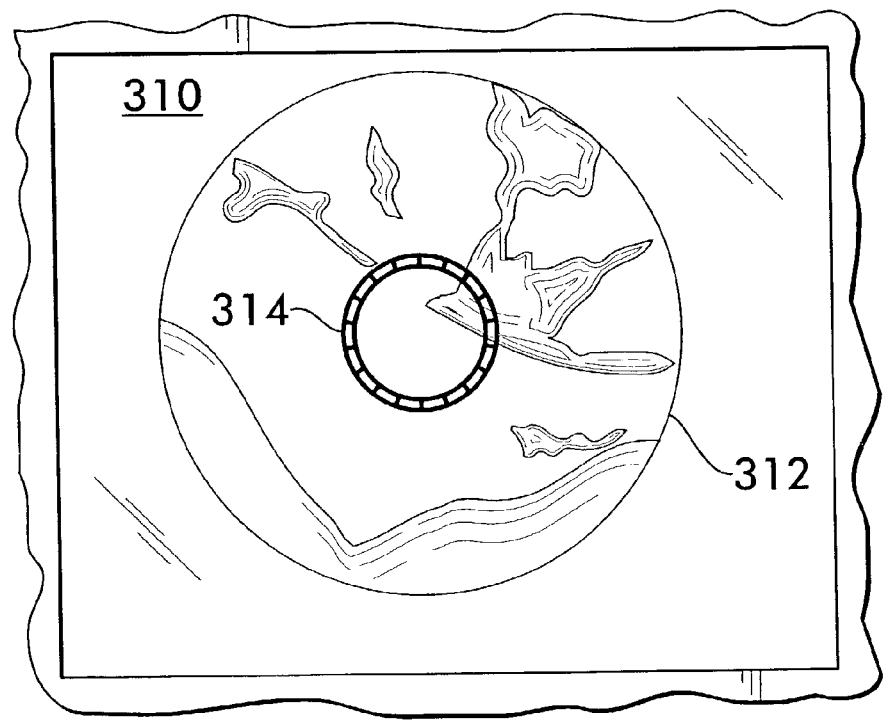

With reference to FIGS. 2, 3A, and 3B, in a preferred embodiment, after the reference location is identified, a first view, such as the coarse view 300 depicted in FIG. 3A, is presented to a surgeon on the monitor 118 (FIG. 1) for coarse positioning of the pointer tip 210. Based on instructions from the localization device, the presented view 300, and the surgeon's knowledge of the procedure, the surgeon positions the pointer tip 210 in the general vicinity of the reference location 206, e.g., in the intercondylar fossa of the femur 204.

In the view illustrated in FIG. 3A, a femur image 302 and a targeting system 304 are displayed. The targeting system 304 employs cross hairs 305 and arrows such as a down arrow 306 and a left arrow 308 to guide the surgeon in positioning the pointer tip 210 to reach the reference location 206. The arrows represent the current position of the pointer tip 210 with reference to the intercondylar fossa of the femur 204. In a preferred embodiment, up and down arrows corresponds to positions right and left, respectively, of the reference location 206 within the intercondylar fossa of the femur 204 (i.e., perpendicular to the displayed femur image 302). For example, the down arrow 306 displayed on the coarse view 300 indicates to the surgeon that the pointer tip 210 is left of the reference location 206 and needs to be moved to the right to reach the reference location 206. In the preferred embodiment, left and right arrows indicate a direction that corresponds to positions below and above, respectively, of the reference location 206 within the intercondylar fossa of the femur 204. For example, the left arrow 308 indicates to the surgeon that the pointer tip 210 is below the reference location 206 and needs to be moved upwards to reach the reference location 206.

In certain embodiment, the femur image 302 in the coarse view 300 remains unchanged in its position and orientation within the coarse view 300. In alternative embodiments, it is contemplated that the position, orientation, and/or magnification of the femur image 302 may change based on the position of the pointer tip 210 relative to the femur 204.

When the pointer tip 210 is moved within a first predefined distance of the reference location 206, e.g., within 2 mm, a second view, such as the fine view 310 depicted in FIG. 3B, is presented to the surgeon on the monitor 118 (FIG. 1). The fine view 310 depicts a magnified view 312 of the surface of the femur 204 surrounding the pointer tip 210 and is used for precise positioning of the pointer tip 210. In the fine view 310, a circle 314 is displayed that represents a virtual tip of a drill bit (not shown) for use in cutting the femoral tunnel. The circle's center corresponds to the pointer tip 210 and represents the center of the drill bit and the circle's diameter represents the diameter of the drill bit.

In one embodiment, the magnified view 312 displayed in the fine view 310 is updated as the pointer tip 210 moves along the surface of the femur 204, with the center of the screen corresponding to the surface of the femur 204 where the pointer tip 210 is positioned. In another embodiment, the center of the screen corresponds to the reference location 206, and the circle 314 moves based on the location of the pointer tip 210 with respect to the reference location 206.

When the fine view 310 is displayed, the surgeon moves the pointer tip 210 in the vicinity of the reference location 206, e.g., within 10 mm, and observes feedback from the localization device corresponding to the current position of the pointer tip 210 relative to the reference location 206 to determine the optimum location for the femoral tunnel. Preferably, the circle 314 displayed in the fine view 310 changes color depending on the isometricity of the location being identified with the pointer tip 210 as calculated by the localization device based on a previously drilled tibial tunnel (described above in detail). For example, if the isometricity is less than or equal to 1.5 mm, the circle is displayed in green; less than or equal to 2.5 mm but greater than 1.5 mm, the circle is displayed in yellow; and greater than 2.5 mm, the circle is displayed in red. The surgeon selects the optimum location for the femoral tunnel based on the observed isometricity, other information available from the localization device, and plausibility in the mind of the surgeon based on his/her training and experience. The surgeon causes the localization device 110 to record the selected point by placing the pointer tip 210 on the selected optimum location and instructing the localization device 110 to record the point such as by operating a foot pedal 115.

After the pointer tip 210 is positioned within the first predefined distance of the reference location 206 and the fine view 310 is displayed, the view will not revert back to the coarse view 300 until the pointer tip is positioned further than a second predefined distance from the reference location 206, e.g., further than about 10 mm. Preferably, the first and second predefined distances are different, with the second distance being greater than the first distance to prevent rapid switching between views when the pointer tip 210 is located in the vicinity of the first or second predefined distances from the reference location 206. For example, when in the coarse view 300 and the pointer tip 210 passes within the first predefined distance (e.g., 2 mm) of the reference location 206, the view will switch from the coarse view 300 to the fine view 310. However, when in the fine view 310, the view will not switch back to the coarse view 300 until the pointer tip 210 is further away from the reference location 206 than the second predefined distance (e.g., 10 mm), rather than the first predefined distance (e.g., 2 mm). Accordingly, when the view switches from the coarse view 300 to the fine view 310 upon the pointer tip 210 passing within 2 mm of the reference location 206, the view will not switch as the pointer tip 210 moves to 3 mm and back to within 2 mm, thereby avoiding rapid switching back and forth between views.

FIG. 4 depicts a flow chart 400 for determining which of the first and second views (FIGS. 3A and 3B) is displayed on the monitor 118 of the localization device 110 of FIG. 1. At block 402, a reference location 206 (FIG. 2) is identified by a localization device.

At block 404, the distance between a pointer tip 210 (FIG. 2) and the reference location 206 is monitored by the localization device. In a preferred embodiment, the localization device monitors the distance by repeatedly calculating the magnitude of a vector extending between the reference location 206 and the present position of the pointer tip 210. The distance is continuously updated to reflect the current distance between the pointer tip and the reference location throughout the rest of the steps of flow chart 400.

At block 406, a first view, e.g., the coarse view 300 of FIG. 3A, is displayed by the localization device on a monitor.

At block 408, the monitored distance determined according to block 404 is compared to a first predefined distance (e.g., about 2 mm). If the determined distance is greater than the first predefined distance, processing proceeds to block 406 and the first view continues to be displayed. If the determined distanced is less than the first predefined distance, processing proceeds to block 410 and the second view, e.g., the fine view 310 of FIG. 3B, is displayed.

At block 412, the monitored distance determined according to block 404 is compared to a second predefined distance (e.g., about 10 mm). If the determined distance is less than the second predefined distance, processing proceeds to block 410 and the second view continues to be displayed. If the determined distanced is greater than the second predefined distance, processing proceeds to block 406 and the first view, e.g., the coarse view 300 of FIG. 3A, is displayed.

The programming to accomplish the steps set forth in the flow chart 400 of FIG. 4 will be readily apparent to those skilled in the art. In addition, it will be recognized by those skilled in the art that the steps depicted in FIG. 4 may be performed by a computer running computer readable program code embodied in a computer readable medium. Alternatively, the present invention may be implemented by a state machine, digital signal processor, processor, microprocessor, microcontroller, or essentially any processing circuit for performing instructions.

In an alternative embodiment, time is a factor in determining when to switch between display screens. When in a first view and the pointer tip 210 is moved within a first predefined distance of the reference location 206, e.g., within 2 mm, for more than a predefined period of time, e.g., 0.1 sec, a second view is presented to the surgeon on the monitor 118 (FIG. 1). If the pointer tip 210 is within the first predefined distance of the reference location 206 only momentarily, e.g., for less than 0.1 sec, the first view will continue to be presented to the surgeon. Likewise, when in a second view and the pointer tip 210 is moved further away than a second predefined distance of the reference location 206, e.g., 10 mm, for a predefined period of time, e.g., 0.1 sec, the first view is presented to the surgeon on the monitor 118 (FIG. 1). If the pointer tip 210 is further away than the second predefined distance of the reference location 206 momentarily, e.g., for less than 0.1 sec, the second view will continue to be presented to the surgeon. This embodiment minimizes the effect of inadvertent movements, such as a muscle twitch.

Although the present invention is described in connection with a procedure for drilling a femoral tunnel, it is contemplated that the present invention may be used to refine screen displays wherever the distance between a reference location and a pointer tip are known. In addition, although the present invention has been described using two display screen (i.e., having two display modes, e.g., coarse and fine), it will be readily apparent to those skilled in the art that essentially any number of display modes may be used. For example, a plurality of display screens providing different amounts of magnification may be employed, e.g., magnification of 1×, 5×, 10×, etc.

Having thus described a few particular embodiments of the invention, various alterations, modifications, and improvements will readily occur to those skilled in the art. Such alterations, modifications and improvements as are made obvious by this disclosure are intended to be part of this description though not expressly stated herein, and are intended to be within the spirit and scope of the invention. Accordingly, the foregoing description is by way of example only, and not limiting. The invention is limited only as defined in the following claims and equivalents thereto.

What is claimed is:

1. A method of generating a display of a localization device, the localization device identifying a reference location, the method comprising the steps of:
    monitoring the distance between a pointer and said reference location with said localization device; and
    displaying a first one of a plurality of views based on said monitored distance with said localization device,
    wherein said displaying step comprises the steps of:
        displaying a first of said plurality of views with said localization device;
        switching from said first view to a second of said plurality of views with said localization device when said pointer tip is less than a first distance from said reference location; and
        switching from said second view to said first view with said localization device when said pointer tip is greater than a second distance from said reference location,
        wherein said first and second distances are different.

2. The method of claim 1, wherein said monitoring step comprises at least the step of:
    calculating the magnitude of a vector extending between said pointer tip and said reference location.

3. The method of claim 2, wherein said monitoring step further comprises at least the step of:
    tracking said pointer tip with the localization device.

4. The method of claim 1, wherein, when displayed, said first and second views are displayed on a monitor associated with the localization device.

5. The method of claim 1, wherein said first distance is about 2 millimeters and said second distance is about 10 millimeters.

6. The method of claim 1, wherein said second view has a greater magnification than said first view.

7. The method of claim 1, wherein said first view comprises at least:
    a targeting system comprising displayable arrows indicating the direction said pointer tip has to travel to reach said reference location.

8. The method of claim 7, wherein said first view further comprises at least:
    an image of an object associated with said reference location.

9. The method of claim 1, wherein said second view comprises at least:
    a magnified view of a surface in the vicinity of said reference location; and
    a virtual guide at the center of said second view, the center of said second view corresponding to said pointer tip.

10. The method of claim 9, wherein said virtual guide changes colors based on the distance between said pointer tip and a second reference location determined by the localization device.

11. The method of claim 1, wherein said displaying step comprises at least the steps of:
    displaying a first of said plurality of views;
    switching from said first view to a second of said plurality of views when said pointer tip is less than a first distance from said reference location for a first predefined period of time; and
    switching from said second view to said first view when said pointer tip is greater than a second distance from said reference location for a second predefined period of time.

12. The method of claim 1, wherein said reference location is a location on a femur for drilling a femoral tunnel that will produce the best calculated isometricity.

13. The method of claim 12, further comprising at least the step of:
    selecting an optimum location for drilling a femoral tunnel in the vicinity of said reference location based on feedback from the localization device.

14. The method of claim 1 wherein said second distance is greater than said first distance.

15. The method of claim 14 wherein said first view comprises a first magnification level and said second view comprises a second magnification level and wherein said first magnification level is lesser than said second magnification level.

16. A localization device, said localization device identifying a reference location, said localization device comprising:
    sensors for tracking a marker associated with a pointer tip;
    a monitor; and
    a computer coupled to said sensors and said monitor for monitoring the distance between said pointer tip and said reference location and selecting a view for display on said monitor from a plurality of views based on the monitored distance,
    wherein said computer comprises:
    means for displaying a first of said plurality of views;
    means for switching from said first view to a second of said plurality of views when said pointer tip is less than a first distance to said reference location; and
    means for switching from said second view to said first view when said pointer tip is greater than a second distance from said reference location:
    wherein said first and second distances are different.

17. The device of claim 16, wherein said computer comprises at least:
    means for calculating the magnitude of a vector extending between said pointer tip and said reference location.

18. The device of claim 16, wherein said second view has a greater magnification than said first view.

19. The device of claim 16, wherein said first view comprises at least:
    a targeting system comprising displayable arrows indicating the direction said pointer tip has to travel to reach said reference location.

20. The device of claim 16, wherein said second view comprises at least:
    a magnified view of a surface in the vicinity of said reference location centered around the location of said pointer tip.

21. The device of claim 16, wherein said computer comprises at least:

means for displaying a first of said plurality of views;

means for switching from said first view to a second of said plurality of views when said pointer tip is less than a first distance to said reference location for a first predefined period of time; and means for switching from said second view to said first view when said pointer tip is greater than a second distance from said reference location for a second predefined period of time.

22. The device of claim 16, wherein said reference location is a location on a femur for drilling a femoral tunnel that has the best calculated isometricity.

23. The localization device of claim 16 wherein said second distance is greater than said first distance.

24. The localization device of claim 23 wherein said first view comprises a first magnification level and said second view comprises a second magnification level and wherein said first magnification level is lesser than said second magnification level.

25. A computer program product for displaying views in a localization device, said localization device identifying a reference location, said computer program product comprising:

computer readable medium having computer instructions for:

monitoring the distance between a pointer tip and said reference location; and displaying one of a plurality of views based on said monitored distance;

switching from said first view to a second of said plurality of views when said pointer tip is less than a first distance to said reference location; and switching from said second view to said first view when said pointer tip is greater than a second distance from said reference location, wherein said first and second distances are different.

26. The product of claim 25, wherein said computer medium further comprises:

computer instructions for calculating the magnitude of a vector extending between said pointer tip and said reference location.

27. The product of claim 25, wherein said computer medium further comprises computer instructions for:

displaying a first of said plurality of views;

switching from said first view to a second of said plurality of views when said pointer tip is less than a first distance to said reference location for a first predefined period of time; and switching from said second view to said first view when said pointer tip is greater than a second distance from said reference location for a second predefined period of time.

28. The product of claim 25 wherein said second distance is greater than said first distance.

29. The product of claim 28 wherein said first view comprises a first magnification level and said second view comprises a second magnification level and wherein said first magnification level is lesser than said second magnification level.

\* \* \* \* \*